United States Patent
Biedermann et al.

(10) Patent No.: US 8,828,060 B2
(45) Date of Patent: **\*Sep. 9, 2014**

(54) ELEMENT WITH A SHANK AND A HOLDING ELEMENT CONNECTED TO IT FOR CONNECTING TO A ROD

(75) Inventors: Lutz Biedermann, VS-Villingen (DE); Jürgen Harms, Karlsruhe (DE)

(73) Assignee: Biedermann Technologies GmbH & Co. KG, Donaueschingen (DE)

( * ) Notice: Subject to any disclaimer, the term of this patent is extended or adjusted under 35 U.S.C. 154(b) by 0 days.

This patent is subject to a terminal disclaimer.

(21) Appl. No.: 10/306,057

(22) Filed: Nov. 27, 2002

(65) Prior Publication Data

US 2003/0100896 A1    May 29, 2003

(30) Foreign Application Priority Data

Nov. 27, 2001    (DE) .................................. 101 57 969

(51) Int. Cl.
 *A61B 17/70*    (2006.01)
(52) U.S. Cl.
 USPC .......................................................... 606/270
(58) Field of Classification Search
 USPC .................. 606/61, 73, 601, 72; 411/436
 See application file for complete search history.

(56) References Cited

U.S. PATENT DOCUMENTS

| | | | | |
|---|---|---|---|---|
| 2,005,348 A | * | 6/1935 | Michell ........................ | 411/436 |
| 2,005,995 A | * | 6/1935 | Knox ............................ | 417/400 |
| 2,268,576 A | * | 1/1942 | Drewett ........................ | 403/365 |
| 2,514,589 A | * | 7/1950 | Penman ........................ | 411/423 |
| 2,684,168 A | * | 7/1954 | McGinnis et al. ........... | 215/330 |
| 2,783,809 A | | 3/1957 | Haines et al. | |
| 3,949,769 A | * | 4/1976 | Minka ........................... | 132/324 |
| 4,369,011 A | * | 1/1983 | Ploss ............................ | 411/223 |

(Continued)

FOREIGN PATENT DOCUMENTS

| | | | | |
|---|---|---|---|---|
| DE | 299 03 342 U1 | 2/1999 | ............ | A61B 17/70 |
| DE | 298 10 798 U1 | 12/1999 | | |

(Continued)

OTHER PUBLICATIONS

Product information for Medtronic Sofamor Danek; CD Horizon Legacy 5.5 Spinal System dated 2003.

(Continued)

*Primary Examiner* — Anu Ramana
(74) *Attorney, Agent, or Firm* — Christie, Parker & Hale, LLP (57) ABSTRACT

An element with a shank (1) and a holding element (2) connected to it for connecting to a rod (100) is provided. The holding element (2) has a recess (3) having a U-shaped cross-section for receiving the rod (100) with two legs (4, 5) open at one end (6) and an inner thread (7) on the open legs (4, 5) and a locking element (9) with an outer thread (8) which cooperates with the inner thread of the legs, wherein the inner thread (7) of the legs and the outer thread (8) of the locking element are constructed with a flat thread in which the two flanks (7a, 7b; 8a, 8b)) enclose an angle of 90° in each case with the screw axis (S, M). This prevents splaying of the open legs when the locking element is screwed in. The flat thread is easy to produce.

10 Claims, 4 Drawing Sheets

(56) References Cited

U.S. PATENT DOCUMENTS

| | | | |
|---|---|---|---|
| 4,601,491 A * | 7/1986 | Bell et al. ................... | 285/24 |
| 4,688,832 A * | 8/1987 | Ortloff et al. ............ | 285/148.19 |
| 4,846,614 A * | 7/1989 | Steinbock ................. | 411/307 |
| 4,850,775 A | 7/1989 | Lee et al. | |
| 5,005,562 A | 4/1991 | Cotrel ....................... | 128/69 |
| 5,092,635 A * | 3/1992 | DeLange et al. .......... | 285/334 |
| 5,536,268 A | 7/1996 | Griss | |
| 5,605,457 A | 2/1997 | Bailey et al. | |
| 5,605,458 A | 2/1997 | Bailey et al. | |
| 5,607,304 A | 3/1997 | Bailey et al. | |
| 5,782,833 A | 7/1998 | Haider ....................... | 606/61 |
| 5,810,818 A | 9/1998 | Errico et al. ............... | 606/61 |
| 5,817,094 A | 10/1998 | Errico et al. ............... | 606/61 |
| 5,858,020 A * | 1/1999 | Johnson et al. ............ | 623/23.15 |
| 6,063,090 A | 5/2000 | Schlaepfer | |
| 6,074,391 A * | 6/2000 | Metz-Stavenhagen et al. | 606/61 |
| 6,183,472 B1 | 2/2001 | Lutz | |
| 6,224,598 B1 * | 5/2001 | Jackson ..................... | 606/61 |
| 6,315,564 B1 * | 11/2001 | Levisman .................. | 433/174 |
| 6,454,768 B1 | 9/2002 | Jackson | |
| 6,485,220 B2 * | 11/2002 | Hecht ........................ | 403/343 |
| 6,485,491 B1 | 11/2002 | Farris et al. ............... | 606/61 |
| 6,488,681 B2 | 12/2002 | Martin et al. .............. | 606/61 |
| 6,726,687 B2 * | 4/2004 | Jackson ..................... | 606/61 |
| 6,730,089 B2 | 5/2004 | Jackson ..................... | 606/61 |
| 7,018,378 B2 | 3/2006 | Biedermann et al. | |

FOREIGN PATENT DOCUMENTS

| | | |
|---|---|---|
| DE | 199 12 364 A1 | 10/2000 |
| EP | 0 614 649 A1 | 9/1994 |
| JP | 8 112291 | 5/1996 |
| SU | 371 359 A | 2/1973 |
| SU | 371359 | 2/1973 |
| WO | WO 95/01132 A | 1/1995 |
| WO | WO 00/27297 | 5/2000 |

OTHER PUBLICATIONS

Title pages of the 26th Edition of the Machinery's Handbook and pp. 1706 and 1816-1818.

Title page of the 21st Edition of the Machinery's Handbook and pp. 1336-1339.

Title pages of the 22nd Edition of the Machinery's Handbook and pp. 1324-1327.

Title pages of the 22nd Edition of the Machinery's Handbook and p. 1206.

Title page of the 27th Edition of the Machinery's Handbook and pp. 1846-1850.

United States Court of Appeals for the Federal Circuit, Opening Brief for Lutz Biedermann and Jurgen Harms, dated Jan. 28, 2013 for Appeal No. 2013-1080 (U.S. Appl. No. 10/306,057), 59 pages.

United States Court of Appeals for the Federal Circuit, Brief for Appellee, dated Apr. 8, 2013 for Appeal No. 2013-1080 (U.S. Appl. No. 10/306,057), 36 pages.

United States Court of Appeals for the Federal Circuit, Reply Brief for Lutz Biedermann and Jurgen Harms, dated May 9, 2013 for Appeal No. 2013-1080 (U.S. Appl. No. 10/306,057), 23 pages.

United States Court of Appeals for the Federal Circuit, Decision, dated Oct. 18, 2013 for Appeal No. 2013-1080 (U.S. Appl. No. 10/306,057), 17 pages.

Information from Machinery's Handbook provided by Chris McCauley, editor of Machinery's Handbook on Feb. 24, 2014, 3 pages.

Office action for U.S. Appl. No. 13/483,792, dated Oct. 3, 2012, 7 pages.

Final Rejection for U.S. Appl. No. 13/483,792, dated Jul. 15, 2013, 5 pages.

* cited by examiner

ELEMENT WITH A SHANK AND A HOLDING ELEMENT CONNECTED TO IT FOR CONNECTING TO A ROD

BACKGROUND OF THE INVENTION

1. Field of the Invention

The invention relates to an element to be used in spinal column surgery or accident surgery with a shank and a holding element connected to it for connecting to a rod.

2. Description of Related Art

A bone screw with a shank and a holding element connected to it for connecting to a rod according to the preamble of claim 1 is known from EP 0 614 649. In this so-called polyaxial bone screw described the inner thread of the open legs of the holding element or receiving part and the outer thread of the inner screw have substantially a rounded thread.

From U.S. Pat. No. 5,005,562 and U.S. Pat. No. 6,074,391 in each case is known an element with a shank and a holding element connected to it for connecting to a rod, wherein the holding element comprises a recess having a U-shaped cross-section for receiving the rod with two legs open at one end and an inner thread on the open legs and a locking element with an outer thread which cooperates with the inner thread of the legs. The inner thread of the open legs of the holding element or receiving part and the outer thread of the inner screw are constructed with a saw-tooth pitch to avoid splaying of the legs by radially acting forces during screwing in.

An element with a shank and a holding element connected to it for connecting to a rod, wherein the holding element comprises a recess having a U-shaped cross-section for receiving the rod with two legs open at one end and an inner thread on the open legs and a locking element with an outer thread which cooperates with the inner thread of the legs is also known from WO 00/27 297. In this element the flanks of the inner thread facing away from the open ends of the legs formed by the U-shaped recess enclose a negative angle with a plane perpendicular to the central axis of the receiving part. This is also intended to prevent splaying of the legs.

In the above-described devices either a device encircling the holding element from outside is required to prevent splaying of the legs or the thread to be used is difficult to produce. This applies in particular to the thread known from WO 00/27 297 with the negative flank angle.

It is the object of the invention to provide an element with a shank and a holding element connected to it for connecting to a rod, which is easy to produce, compact in structure and easy to handle.

SUMMARY OF THE INVENTION

The present invention provides an element with a shank (1) and a holding element (2; 21; 21') connected to it for connecting to a rod (100), wherein the holding element (2; 21; 21') comprises a recess having a U-shaped cross-section for receiving the rod with two legs (4, 5; 26, 27) open at one end (6; 28) and an inner thread (7; 29) on the open legs and a locking element (9; 34; 50; 50') with an outer thread (8; 35; 51) which cooperates with the inner thread of the legs, characterised in that the two flanks (7a, 7b) of the inner thread (7; 29) enclose an angle of 90°, respectively, with the central axis (M) of the holding element.

Embodiments of the invention include elements having one or more of the following features:

a. the thread cross-section is substantially constructed as rectangular;

b. the locking element (9; 34; 50; 50') cooperating with the inner thread (7; 29) comprises a matching outer thread (8; 35; 51);

c. with unloaded bringing into engagement of the locking element (9; 34; 50; 50') and the open legs (4, 5; 26, 27) of the holding element (2; 21; 21') a gap is provided between the flanks (7b) of the holding element facing away from the open end and the flanks (8a) of the locking element facing the open end;

d. the root (7c) of the inner thread of the open legs is formed, respectively, as rounded;

e. the holding element (2) is formed monoaxially to the shank (1);

f. the locking element (50; 50') is constructed as a nut with an inner thread (52) and an inner screw (60) is provided for screwing into the locking element;

g. the inner thread (52) of the locking element (50; 50') and the outer thread (61) of the inner screw (60) are formed as metric threads;

h. the element has a head (20), which is connected to the shank (1) and polyaxially connected to the holding element (21; 21'), and a pressure element (30; 40) acting on the head (20) is provided for fixing the angle position of the head relative to the holding element;

i. the pressure element (40) comprises on its side facing away from the head (20) a recess (45) open to the open end (28) for receiving the rod (100), the depth of which, seen in the axial direction, is larger than the diameter of the rod (100);

j. the locking element (50; 50') comprises on one of its ends a projection (54) in the radial direction, which acts as stop when the locking element is screwed in between the open legs (26, 27);

k. the projection (54) comprises on its open end a section (55) which cooperates with a corresponding section (56) on the outer side of the holding element (21') and overlaps it like a cap;

l. a section adjacent to the open end of the shank is formed with a bone thread for screwing into the bone or as a hook; and m. the two flanks (7a, 7b) of the inner thread are constructed without undercuts or steps;

The invention further provides an element with a shank (1) and a holding element (2; 21; 21') connected to it for connecting to a rod (100), wherein the holding element (2; 21; 21') comprises a recess having a U-shaped cross-section for receiving the rod with two legs (4, 5; 26, 27) open at one end (6; 28) and an inner thread (7; 29) on the open legs and a locking element (9; 34; 50; 50') with an outer thread (8; 35; 51) which cooperates with the inner thread of the legs, characterised in that the two flanks (7a, 7b) of the inner thread (7; 29) enclose an angle of 90°, respectively, with the central axis (M) of the holding element and wherein the two flanks (7a, 7b) of the inner thread are formed without undercuts or steps.

The element according to the invention has the advantage that the inner thread of the legs or the outer thread of the locking element, constructed as a flat thread, is extremely easy to produce. This saves production costs and precision can be increased. As with this thread no forces act outwards in the radial direction, splaying of the open legs of the holding element is avoided and therefore no additional element to be applied from outside to avoid splaying is required. This enables a more compact structure.

Further features and advantages of the invention emerge from the description of embodiment examples using the figures.

BRIEF DESCRIPTION OF THE DRAWINGS

FIG. 2b shows an enlarged illustration of a detail from FIG. 2a.

FIG. 3b shows an enlarged illustration of a detail from FIG. 3a.

DETAILED DESCRIPTION OF THE PREFERRED EMBODIMENTS

Figure 1:
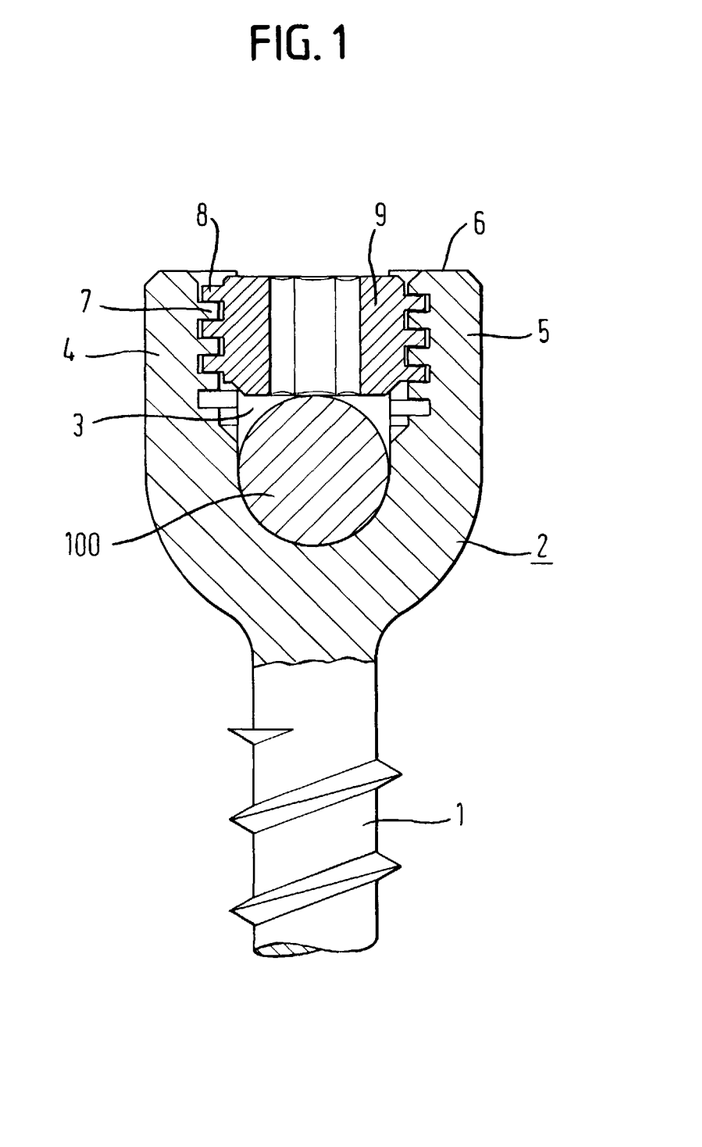
FIG. 1 shows a sectional illustration of a first embodiment of the element according to the invention.

The element according to the invention is constructed in the embodiment illustrated in FIG. 1 of the figures as a monoaxial bone screw. It has a shank 1 with a bone thread section and a receiving part 2, rigidly connected to it, for receiving a rod 100 connecting the bone screw to further bone screws. For this purpose the receiving part is provided with a recess 3 with a U-shaped cross-section, which is dimensioned just large enough for the rod 100 to be placed in it and fit into the bottom of the recess. By the U-shaped recess 3 two open legs 4, 5 are formed with in each case one open end 6 forming the upper edge of the receiving part 2. Adjacent to the open end 6 the legs 4, 5 have an inner thread 7, which cooperates with a corresponding outer thread 8 of an inner screw 9, to be screwed in between the legs 4, 5, to fix the rod 100.

As can be seen in particular in FIGS. 1 to 3b, the inner thread 7 and, corresponding to this, the outer thread 8 is constructed as a flat thread. This is characterised in that the thread flanks 7a, 7b of the inner thread enclose in each case an angle of 90° with the central axis M of the receiving part. Correspondingly, thread flanks 8a, 8b of the outer thread of the inner screw 9 enclose an angle of 90° with the screw axis S. The thread cross-section is substantially rectangular. The edges can further be constructed as rounded. The thread flanks are constructed without undercuts.

As emerges in particular from the enlarged illustration according to FIG. 2b and FIG. 3b, in this embodiment example the inner thread 7 of the legs and the outer thread 8 of the inner screw 9 are dimensioned relative to one another as follows: radius $r_1$ from the screw axis S to the root of the thread 8c of the inner screw 9 is smaller than radius $r_2$ from the central axis M of the receiving part 2 to its crest 7d. Radius $r_3$ from the screw axis S to the crest 8d of the inner screw 9 is smaller than radius $r_4$ from the central axis M of the receiving part 2 to the root of the thread 7c of its inner thread.

Figure 2A:
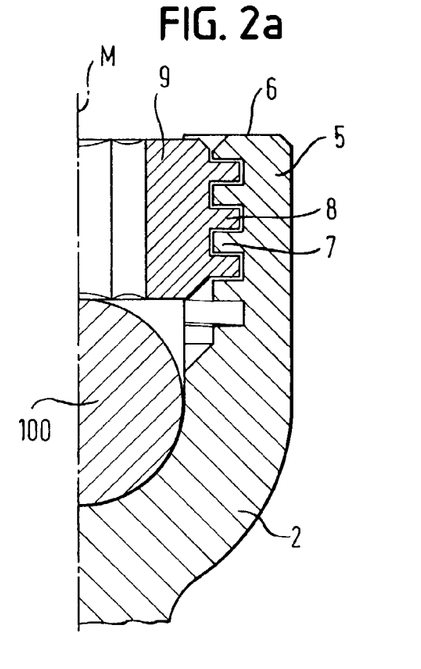
FIG. 2a shows a partial view of the embodiment of FIG. 1 with the inner screw not yet tightened.
Figure 2B:
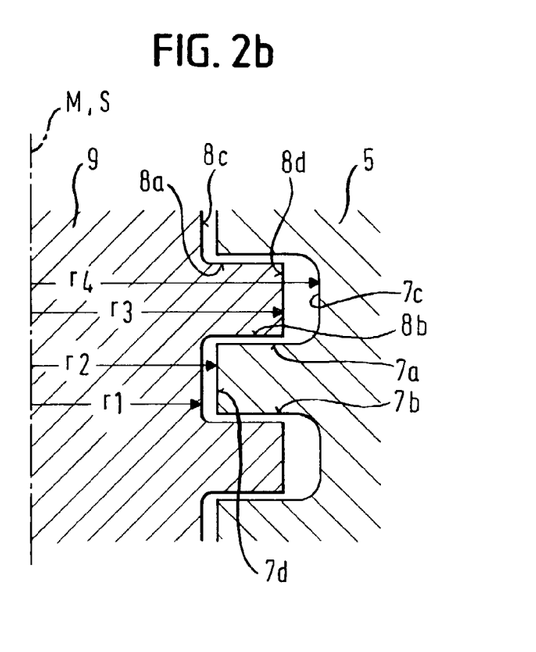
Figure 3A:
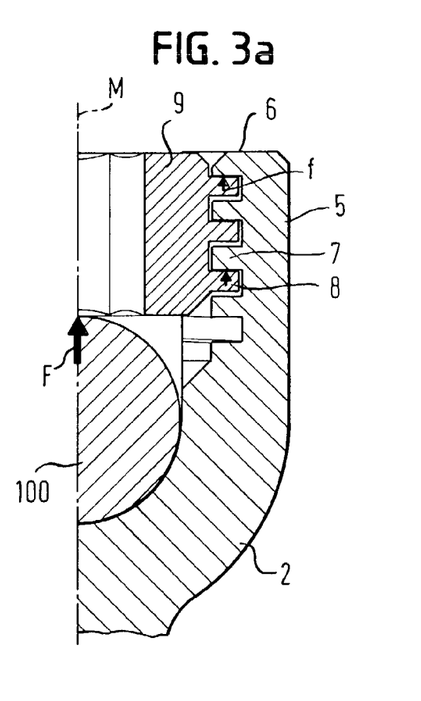
FIG. 3a shows a partial view of the embodiment of FIG. 1 with the inner screw tightened.
Figure 3B:
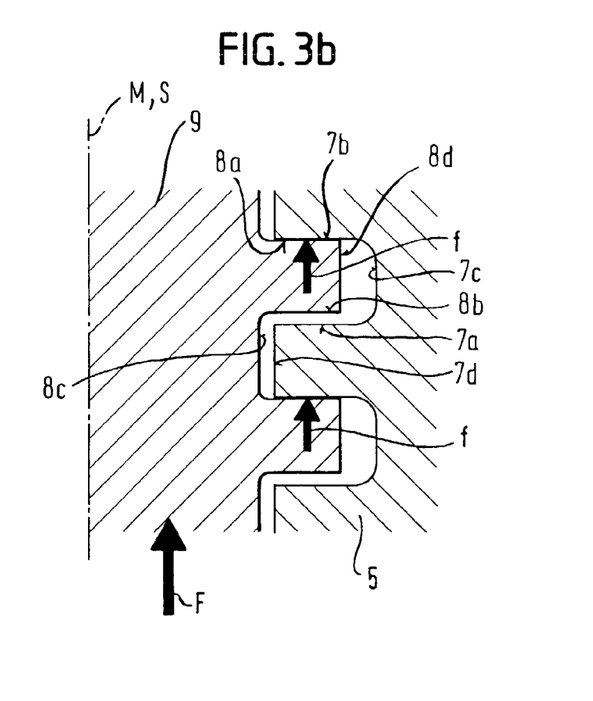

Furthermore, as shown in FIG. 2b, the dimensions of the thread are such that on unloaded bringing into engagement of inner screw and open legs 4, 5 of the receiving part there is a difference between radii $r_1$ and $r_2$, i.e. a radial play, of 1% to 5% of the outer diameter of the thread, preferably approximately 1%. In the axial direction there is, for a recess of approximately 5 mm, an axial play of approximately 10%.

In operation, after the rod has been placed into the receiving part 2, the inner screw 9 is first loosely screwed in, so that the rod can still be adjusted. To fix the rod 100, the inner screw 9 is tightened. It thereby experiences a counterforce, represented in FIGS. 3a and 3b by the arrow F. As a result flanks 8a of the outer thread facing the open end 6, and flanks 7b of the inner thread facing away from the open end come to be on top of one another. The force acting on the thread flanks therein acts only in the axial direction, as illustrated by the short arrows f in FIGS. 3a and 3b. Therefore there is no splaying of the legs 4, 5.

Figure 4:
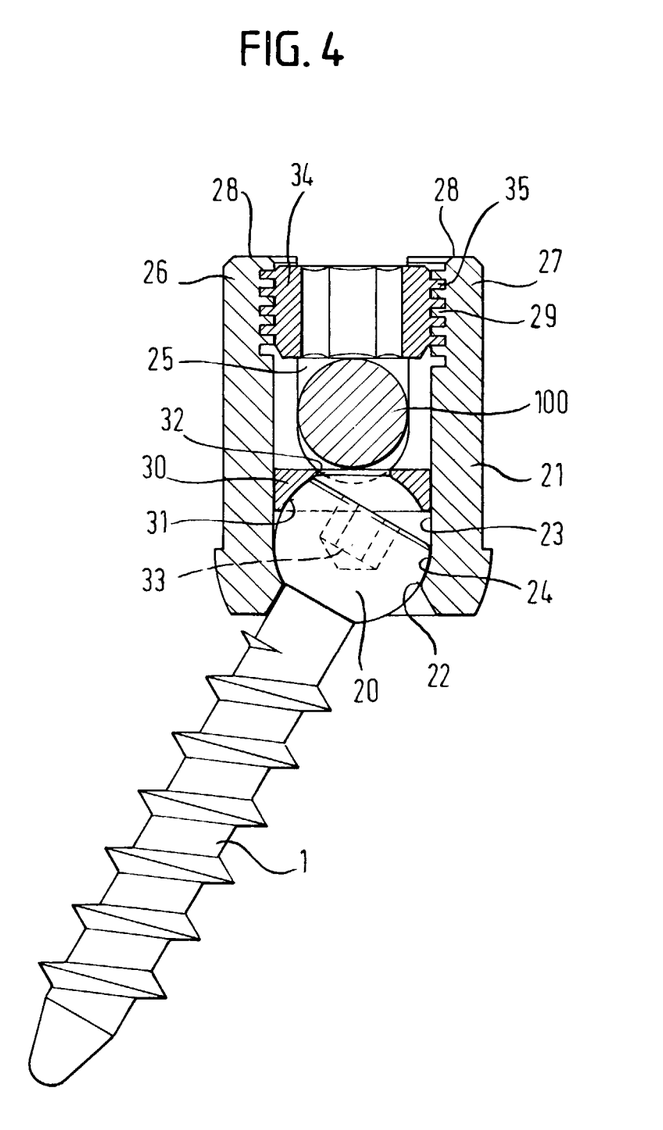
FIG. 4 shows a sectional illustration of a second embodiment.

In a second embodiment shown in FIG. 4 the element according to the invention is constructed as a polyaxial bone screw. The polyaxial bone screw has a screw element with a thread shank 1 with a bone thread which is connected to a receiving part 21 via a head 20, shaped like a segment of a sphere. The receiving part 21 has on one of its ends a first bore 22, aligned symmetrically to the axis, the diameter of which is larger than that of the thread section of the shank 1 and smaller than that of the head 20. The receiving part 21 further has a coaxial second bore 23, which is open at the end opposite to the first bore 22 and the diameter of which is large enough for the screw element to be inserted through the open end with its thread section through the first bore 22 and with its head 20 as far as the bottom of the second bore 23. Between the first and the second bore a small coaxial section 24 is provided which is immediately adjacent to the first bore 22 and is constructed as spherical towards the open end, the radius being substantially identical to the section of the head 20 shaped like a segment of a sphere. Receiving part 21, like receiving part 2 of the first embodiment, has a U-shaped recess 25, arranged as symmetrical to the centre of the part, the bottom of which is directed towards the first bore 22 and by which two open legs 26, 27 are formed, the open end 28 of which forms the upper edge of the receiving part 21. In an area adjacent to the open end 28 the legs 26, 27 have an inner thread 29. The inner thread is constructed according to the invention as a flat thread, as described for the first embodiment.

Further provided is a pressure element 30, which is constructed in such a way that it has on its side facing the head 20 a spherical indentation 31, the radius of which is substantially identical to the radius of the section of the head 20 shaped like a segment of a sphere. The outer diameter of the pressure element is chosen in such a way that the pressure element can perform a sliding movement in the receiving part 21, in other words is displaceable towards the head 20. The pressure element further has a coaxial bore 32 for access to a recess 33 in the screw head 20 for bringing into engagement with a screwing in tool.

To fix the rod 100 and the head in its angle position an inner thread 34 is provided, similarly to in the first embodiment, which has an outer thread 35 cooperating with the inner thread 29 of the legs. The outer thread is again constructed as a flat thread, as in the first embodiment.

In operation the screw element is screwed into the bone after being placed in the receiving part 21. The pressure element 30 and the rod 100 are then inserted in turn. At this stage the screw head 20 is still swivellable. By screwing in the inner thread 34 the screw element and the receiving part 21 are fixed to one another and therefore also the rod 100. As, owing to the construction of the cooperating thread of the legs and the inner screw as flat thread no splaying of the legs takes place, no additional securing is required, whereby the polyaxial screw can be configured compactly and produced at a reasonable price.

Figure 5:
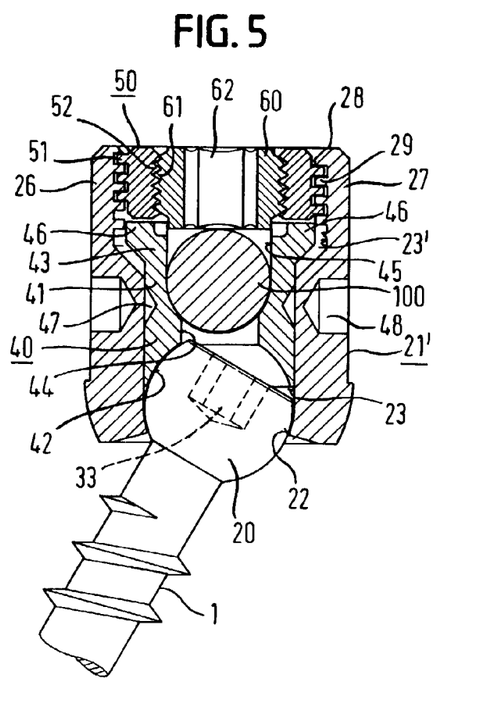
FIG. 5 shows a sectional illustration of a third embodiment.
Figure 6:
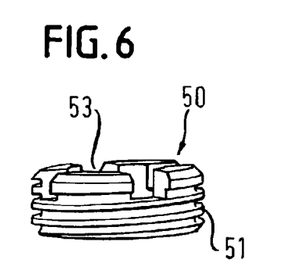
FIG. 6 shows a perspective view of the nut from FIG. 5.

The third embodiment illustrated in FIGS. 5 and 6 also shows a polyaxial bone screw. Parts corresponding to the second embodiment are provided with the same reference numerals. The third embodiment differs from the second embodiment in the construction of the receiving part, the pressure element and the inner screw.

The receiving part 21' has, adjacent to its open end 28, a section 23' which has a larger diameter than the second bore 23 and which tapers conically towards the first bore. The construction of the receiving part in respect of the U-shaped recess and the legs 26, 27 is as in the second embodiment. Adjacent to the open end 28 the inner thread 29 is formed in a predetermined area in section 23'. The inner thread is constructed, as in the first and second embodiment, as a flat thread.

The pressure element 40 of this embodiment has a substantially cylindrical first section 41, the outer diameter of which is chosen in such a way that the pressure element can slide in the second bore 23 of the receiving part 21'. In this first section 41a recess 42, shaped like the segment of a sphere and widening towards the end, is provided, the sphere radius of which is chosen in such a way that in a state inserted into the receiving part it partially encircles the head 20 of the screw element. At the opposite end the pressure element 40 is formed in a second section 43 with an outer diameter enlarged compared with the diameter of the first section 41, which is larger than the inner diameter of the bore 23 of the receiving part 21' but smaller than the inner diameter between the legs 26, 27. The second section 43, corresponding to the construction of the receiving part, verges conically into the first section 41. The pressure element 40 further has a central bore 44 extending therethrough. The diameter of the central bore 44 is dimensioned as just large enough for a screw tool to be guided through it for bringing into engagement with the recess 33 provided in the head 20.

A substantial difference from the pressure element of the second embodiment is that the pressure element of the third embodiment is lengthened in the direction of the open end 28 of the legs. For this purpose it has at its end opposite the recess 42 shaped like the segment of a sphere a U-shaped recess 45, wherein the dimensions of the U-shaped recess of the pressure element are such that the rod 100 can be placed in the channel formed thereby. The depth of the U-shaped recess 45, seen in the direction of the cylindrical axis of the receiving part 21', is larger than the diameter of the rod 100 to be received such that the pressure element 40 projects upwards above the rod 100 with lateral legs 46.

The pressure element 40 further has on its outer casing two countersunk bores 47, arranged opposite and offset by 90° from the centre of the U-shaped recess and extending in the radial direction, which cooperate with corresponding crimped bores 48 in the outer casing of the receiving part 21'.

Instead of the inner screw 9 of the first and second embodiment, in the third embodiment a nut 50, which can be screwed in between the legs 26, 27 of the receiving part, is provided with an outer thread 51, which cooperates with the inner thread 29 of the legs. The outer thread 51 of the nut is constructed as a flat thread, like that of the inner thread of the previous embodiments. The inner thread 52 of the nut 50 is a metric thread. As can be seen from FIG. 6, the nut has on one of its ends slits 53 for bringing into engagement with a screw tool.

Further provided is an inner screw or clamping or set screw 60 for screwing into the nut 50, which has a metric outer thread 61 which cooperates with the inner thread 52 of the nut 50. The inner screw 60 has a recess 62 for bringing into engagement with a screw tool.

In operation, as in the second embodiment, first the screw element is put into the receiving part. Then, differently from the second embodiment, the pressure element 40 is inserted and is first held loosely over the countersunk and crimped bores 47, 48. Following this the bone screw is screwed into the bone and the rod 100 then placed in. Thereupon the nut 50 is screwed in, with inner screw 60 at first loosely screwed into it, until the nut impacts on the upper end of the legs 46 and therefore the pressure element 40 presses on the screw head 20, so that it is locked in its position in the receiving part. Owing to the construction of the inner thread 29 of the legs and the outer thread of the nut 50 as flat threads, the nut 50 does not experience any radial force component, but only an axially directed force, which is why no splaying of the legs takes place. The screw head is thus securely locked. Because the legs 46 of the pressure element project above the placed in rod 100, the rod is still displaceable and yet prevented by the nut 50 from falling out or tilting. Finally, the inner screw 60 is tightened until it presses on the rod 100 and fixes it. Fixing the rod thus takes place independently of fixing the head.

In the third embodiment shown in FIGS. 5 and 6 the nut 50 and the inner screw 60 are fully screwed into the receiving part 21'. In the modified embodiment shown in FIGS. 7 and 8 the nut 50' has at the end containing the slits 53 a ring-shaped projection 54, the outer diameter of which corresponds to the outer diameter of the receiving part 21'. The open end of the ring-shaped projection 54 is further constructed like a cap and has an inclined face 55 which, in the state screwed into the receiving part 21', cooperates with a corresponding bevelled face 56 at the open end 28 of the receiving part 21'. The length of the nut 50' in the axial direction is chosen in such a way that in the state fully screwed into the receiving part 21' the nut 50' presses on the pressure element 40 with a predetermined force, the ring-shaped projection 54 acting as a stop to limit this force.

Figure 7:
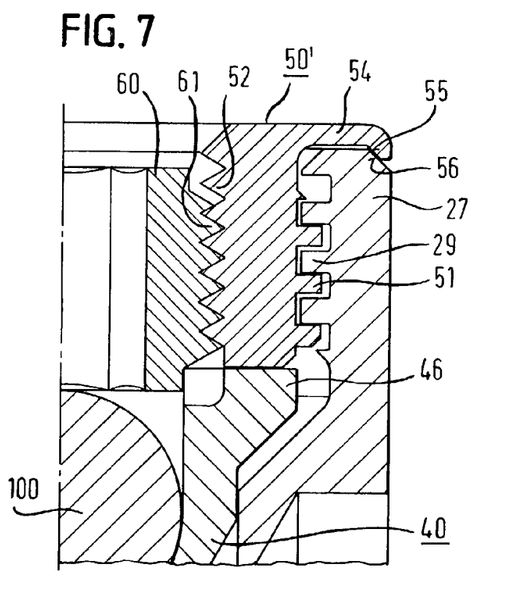
FIG. 7 shows a partial view in section of a modification of the third embodiment.
Figure 8:
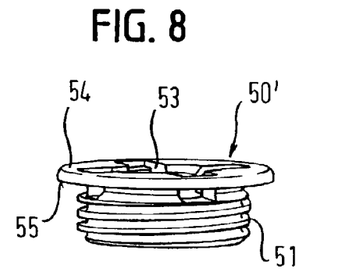
FIG. 8 shows a perspective view of the nut of the embodiment from FIG. 7.

Operation takes place as in the third embodiment with the single difference that the nut 50' can be screwed in only until it rests against the ring-shaped projection 54 and thus the force acting on the pressure element is set to a predetermined value.

To prevent deformation of the legs 26, 27 of the receiving part 21' by axial wringing caused by torsion forces at the moment of tightening, the cap-like projection 54 with its bevelled face 55 grips on to the corresponding bevelled face 56 on the outer face of the receiving part. After final tightening there is no longer any torsional loading of this kind and the legs 26, 27 do not experience any force acting outwards, which could occasion loosening of the nut 50'. Alternatively to the cap-like construction of the projection 54, a ring provided on the screwing in tool can be used.

In a modification of the above-described embodiments a hook is provided instead of the thread shank 1. In a further modification of the polyaxial embodiments, instead of the thread shank 1 or the hook, a bar or a rod-shaped element is provided, which has a head shaped like a segment of a sphere on both ends and is connected to a receiving part of the kind described. In this way an element of this kind can be used as connecting element between two rods 100.

What is claimed is:

1. A bone anchor comprising:
a shank portion;
a holding portion configured to hold a rod; and
a locking element to lock the rod in the holding portion;
wherein the holding portion comprises a recess on one end having a U-shaped cross-section and two open legs for receiving the rod, and an inner thread on the open legs;
wherein the locking element comprises an outer thread having two flanks, the outer thread cooperating with the inner thread, one of the two flanks of the outer thread facing the one end of the holding portion, the other of the two flanks of the outer thread facing away from the one end of the holding portion and each of the two flanks of the outer thread enclosing an angle of 90° with a central axis (M) of the holding portion when the locking element is tightened; and wherein the inner thread comprises two flanks, one of the two flanks of the inner thread facing the one end of the holding portion and the other of the two flanks of the inner thread facing away from the one end of the holding portion, each of the two flanks of the inner thread enclosing an angle of 90° with the central axis (M) of the holding portion;

wherein the thread cross-sections of the inner thread and the outer thread, respectively, are substantially rectangular;

wherein the inner thread of the open legs comprises a rounded root; and wherein a crest of the outer thread of the locking element is spaced from a root of the inner thread when the locking element is tightened.

2. The bone anchor according to claim 1, wherein the locking element cooperating with the inner thread comprises a matching outer thread.

3. The bone anchor according to claim 1, further comprising a gap between the flank of the holding portion facing the one end and the flank of the locking element facing away from the one end when the locking element and the open legs of the holding portion are brought into engagement without a load.

4. The bone anchor according to claim 1, wherein the holding portion is monoaxially formed with the shank portion.

5. The bone anchor according to claim 1, wherein the locking element comprises a nut having a second inner thread and the bone anchor further comprises an inner screw that cooperates with the locking element.

6. The bone anchor according to claim 5, wherein the inner screw comprises a second outer thread and wherein the second inner thread of the locking element and the second outer thread of the inner screw comprise metric threads.

7. The bone anchor according to claim 1, wherein the shank portion is connected polyaxially to the holding portion.

8. The bone anchor according to claim 1, wherein the locking element comprises an end and on the end, a projection in a radial direction, which acts as stop when the locking element is screwed between the open legs.

9. The bone anchor according to claim 8, wherein the projection comprises an end section that cooperates with a corresponding section on the outer side of the holding portion, whereby the projection overlaps the holding portion.

10. The bone anchor according to claim 1, wherein a section of the shank portion comprises a bone thread or a hook.

\* \* \* \* \*

UNITED STATES PATENT AND TRADEMARK OFFICE
CERTIFICATE OF CORRECTION

| | | |
|---|---|---|
| PATENT NO. | : 8,828,060 B2 | Page 1 of 1 |
| APPLICATION NO. | : 10/306057 | |
| DATED | : September 9, 2014 | |
| INVENTOR(S) | : Biedermann et al. | |

It is certified that error appears in the above-identified patent and that said Letters Patent is hereby corrected as shown below:

On the Title Page

(*) Notice, lines 4-5       Delete

"This patent is subject to a terminal disclaimer."

Signed and Sealed this

Fourth Day of November, 2014

Michelle K. Lee
*Deputy Director of the United States Patent and Trademark Office*

UNITED STATES PATENT AND TRADEMARK OFFICE
CERTIFICATE OF CORRECTION

| | | |
|---|---|---|
| PATENT NO. | : 8,828,060 B2 | Page 1 of 1 |
| APPLICATION NO. | : 10/306057 | |
| DATED | : September 9, 2014 | |
| INVENTOR(S) | : Biedermann et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1393 days.

Signed and Sealed this
Third Day of November, 2015

Michelle K. Lee
*Director of the United States Patent and Trademark Office*